(12) United States Patent
Owczarczak

(10) Patent No.: US 7,753,073 B2
(45) Date of Patent: Jul. 13, 2010

(54) OCCLUSION VALVE WITH SAFETY RELIEF

(75) Inventor: John A. Owczarczak, Lancaster, NY (US)

(73) Assignee: Midmark Corporation, Versailles, OH (US)

( * ) Notice: Subject to any disclaimer, the term of this patent is extended or adjusted under 35 U.S.C. 154(b) by 686 days.

(21) Appl. No.: 11/621,603

(22) Filed: Jan. 10, 2007

(65) Prior Publication Data
US 2007/0204922 A1    Sep. 6, 2007

Related U.S. Application Data

(60) Provisional application No. 60/758,023, filed on Jan. 11, 2006.

(51) Int. Cl.
*F16K 7/14* (2006.01)
*F16K 17/168* (2006.01)
(52) U.S. Cl. ............... 137/601.2; 137/539; 251/65; 251/320; 251/331; 128/204.18; 128/207.16
(58) Field of Classification Search ........... 137/601.2, 137/601.21, 539; 251/65, 331, 342, 319, 251/320, 321; 128/204.18, 207.16
See application file for complete search history.

(56) References Cited

U.S. PATENT DOCUMENTS

| 26,844 | A | * | 1/1860 | Hart | 251/331 |
| 232,380 | A | * | 9/1880 | Truesdell | 251/331 |
| 1,844,528 | A | * | 2/1932 | Smith | 251/331 |
| 2,099,841 | A | * | 11/1937 | Connell | 128/205.12 |
| 2,111,430 | A | * | 3/1938 | Lamar | 137/73 |
| 2,211,167 | A | * | 8/1940 | Safford | 251/331 |
| 2,895,497 | A | * | 7/1959 | Jones | 137/316 |
| 3,269,410 | A | * | 8/1966 | Alvarado et al. | 137/882 |
| 3,476,146 | A | * | 11/1969 | Dolter | 137/601.13 |
| 4,016,899 | A | * | 4/1977 | Fletcher | 137/601.2 |
| 4,210,174 | A | * | 7/1980 | Eross | 137/528 |
| 5,107,890 | A | * | 4/1992 | Gute | 137/539 |
| 5,275,086 | A | * | 1/1994 | Stallings, Jr. | 137/539 |
| 5,279,328 | A | * | 1/1994 | Linder et al. | 137/599.01 |

* cited by examiner

*Primary Examiner*—Stephen Hepperle
(74) *Attorney, Agent, or Firm*—Wood, Herron & Evans, LLP

(57) ABSTRACT

An occlusion valve with safety relief comprising a manifold block having an inlet and an outlet. A diaphragm connected to the manifold block and for being manually pressed to stop flow between the inlet and the outlet. A pressure relief valve internal to the manifold block and in fluid communication with downstream and upstream pressures and wherein when the diaphragm is pressed and downstream pressure exceeds a predetermined pressure the pressure relief valve opens allowing flow through the occlusion valve with safety relief.

8 Claims, 13 Drawing Sheets

OCCLUSION VALVE WITH SAFETY RELIEF

The present application claims the filing benefit of U.S. Provisional Application Ser. No. 60/758,023, filed Jan. 11, 2006, the disclosure of which is incorporated herein by reference in its entirety.

BACKGROUND OF THE INVENTION

An anesthesia machine 200, as shown schematically in FIGS. 32 and 33, allows gasses to flow through separate inspiratory and expiratory circuits. The anesthesia machine 200 prevents rebreathing of $CO_2$ by absorbing the $CO_2$ in a bed of absorbent material. The anesthesia machine 200 allows rebreathing of some exhaled gases, and the remaining exhaled gases flow through an exhalation 204 valve and through an adjustable pressure limiting valve (pop off valve) 202 and exit the anesthesia machine 200. The adjustable pressure limiting valve 202 is for providing adequate pressure in the anesthesia machine 200, and in a full open position, the adjustable pressure limiting valve maintains a pressure of about 1-3 centimeters (hereinafter cm) of $H_2O$. During manually assisted ventilation, the adjustable pressure limiting valve is left partially open, and during inspiration a breathing bag is squeezed and pressure increases until the adjustable pressure limiting valve relief pressure is reached.

However, it would be desirable if there were a way to build pressure in the anesthesia machine to a predetermined pressure, while eliminating the possibility of over pressurizing the anesthesia machine.

SUMMARY OF THE INVENTION

The occlusion valve with safety relief includes a manifold block that is positioned between the exhalation valve and the adjustable press pressure limiting valve (hereinafter APL valve). The manifold block is connected to the exhalation valve and the APL valve and is in fluid communication with each. The manifold block has an inlet that leads to an inlet passage that ends at a flow opening. A diaphragm is joined to the manifold block and surrounds the flow opening, such that the flow opening faces the diaphragm. The diaphragm directs the flow of incoming gas between the diaphragm and the surrounding manifold block such that the gas flows through the flow opening to the outlet of the manifold block.

During normal operation, the diaphragm is not pressed and gas flows through the inlet, through the inlet passage and to the flow opening, and from there to the outlet formed in the manifold block. When it is necessary to build downstream pressure, the diaphragm is manually pressed, so that incoming gas cannot flow between the diaphragm and the flow opening. Thus, as a result of pressing the diaphragm, downstream pressure builds which pressurizes the anesthesia machine.

While the diaphragm pressed, if the downstream pressure exceeds a predetermined amount, then a pressure relief valve opens. The pressure relief valve is in fluid communication with downstream and upstream pressure. A set screw having a magnet joined to it is threadably received in the manifold block, and the manifold block has a valve seal or seat spaced a distance from the magnet. The magnetic force of attraction seats a steel ball in the valve seat, thus sealing the pressure relief valve when downstream pressure is below a predetermined amount. When the downstream pressure exceeds the predetermined amount the ball is unseated and gas flows around the steel ball. The gas passes through an escape slot formed in the manifold block, between the diaphragm, which is still pressed against the flow opening, and the surrounding manifold block and out the outlet. Thus, a user can depress the diaphragm to pressurize the anesthesia machine and release it when a desired downstream pressurization of the anesthesia machine is achieved. If the user continues to press the diaphragm, when the predetermined downstream pressure is reached the pressure relief valve automatically opens, and over-pressurization of the anesthesia machine cannot occur. After exiting the manifold block the gas flows to the APL valve.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE PREFERRED EMBODIMENTS

Figure 1:
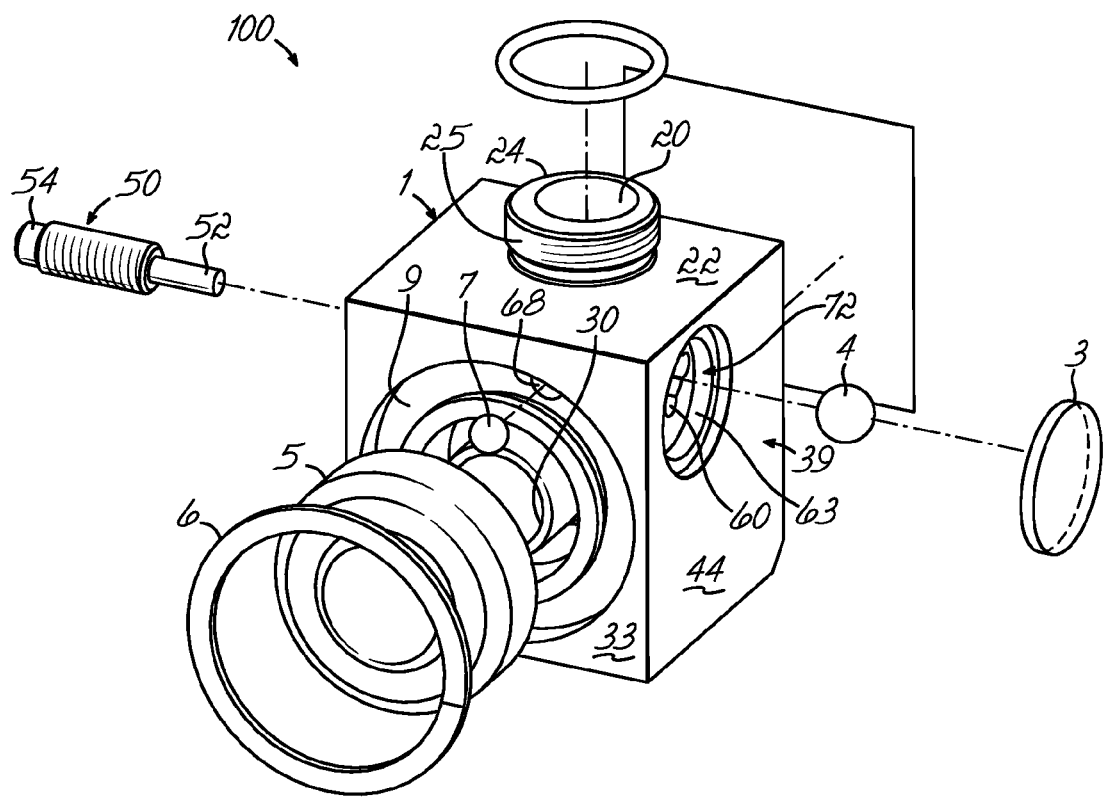
FIG. 1 is an exploded view of the occlusion valve with safety relief.

At the outset, it is pointed out that the dimensions shown in the drawing figures are for illustrative purposes, and it is to be understood that the dimensions of the parts and components of the occlusion valve with safety relief 100 could be otherwise embodied in other preferred embodiments of the invention.

Figure 32:
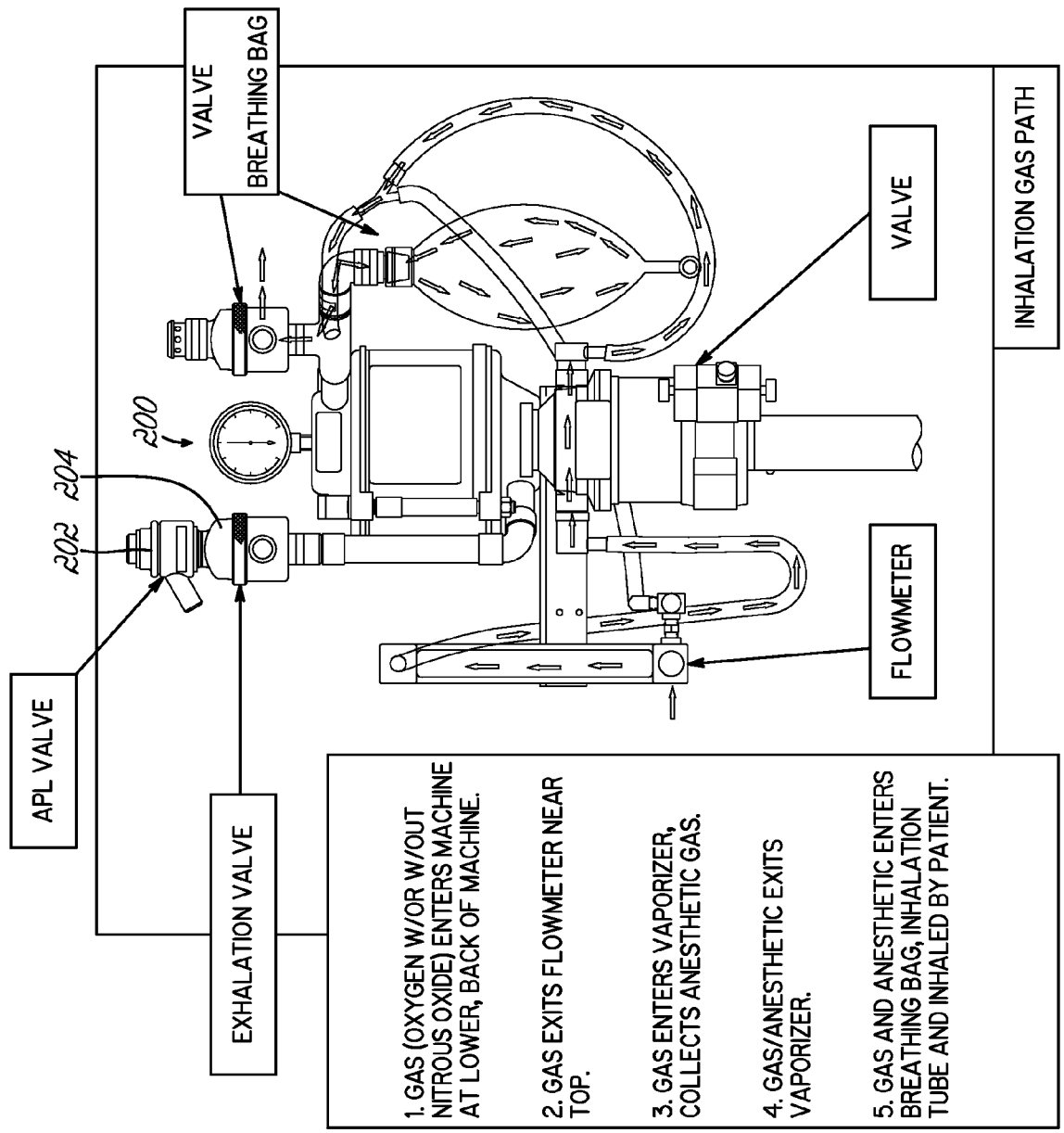
FIG. 32 shows a schematic view of an anesthesia machine (without the occlusion valve having safety relief) during inhalation of gas.
Figure 33:
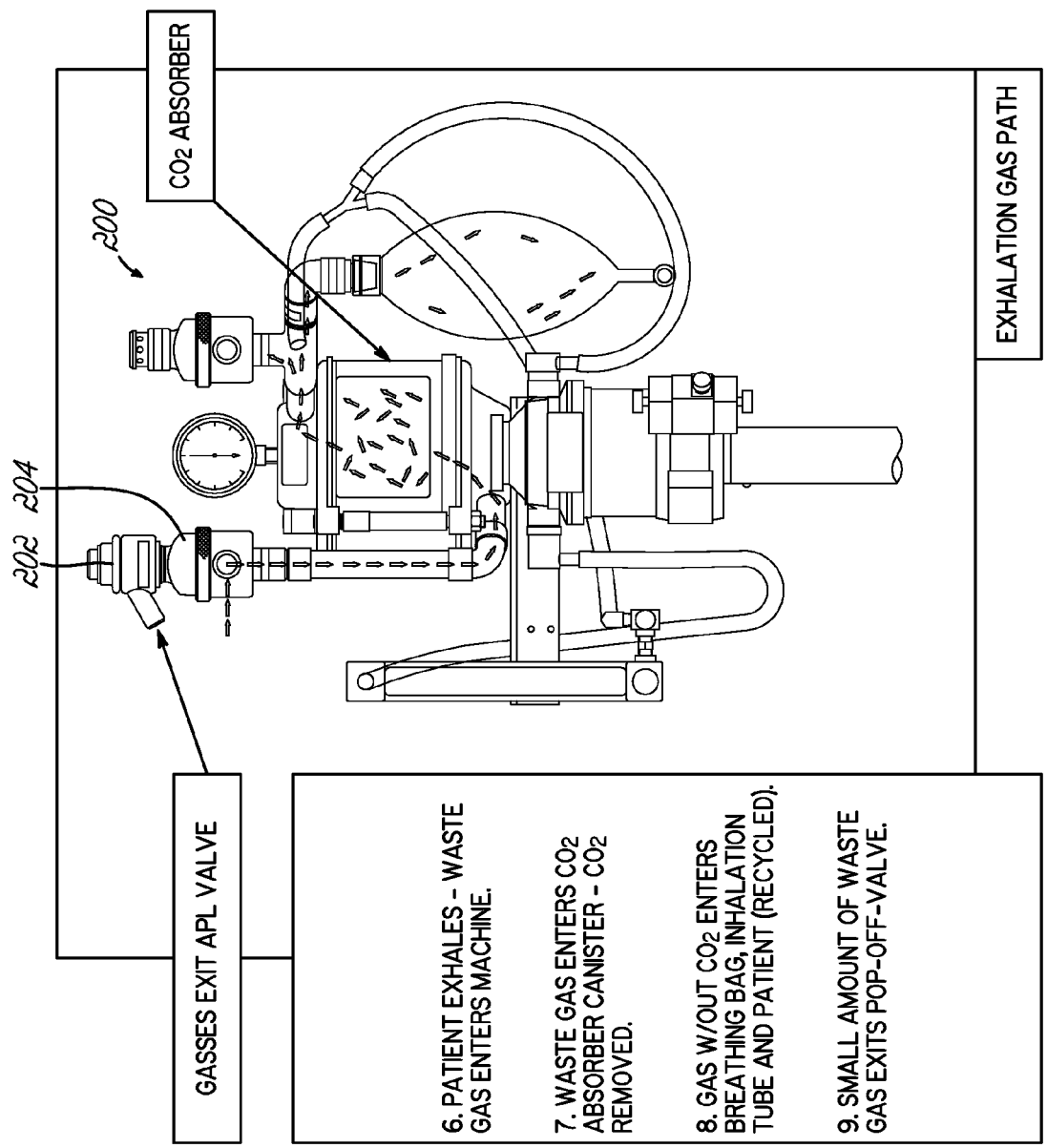
FIG. 33 shows a schematic view of an anesthesia machine (without the occlusion valve with safety relief) during exhalation of gas.
Figure 34:
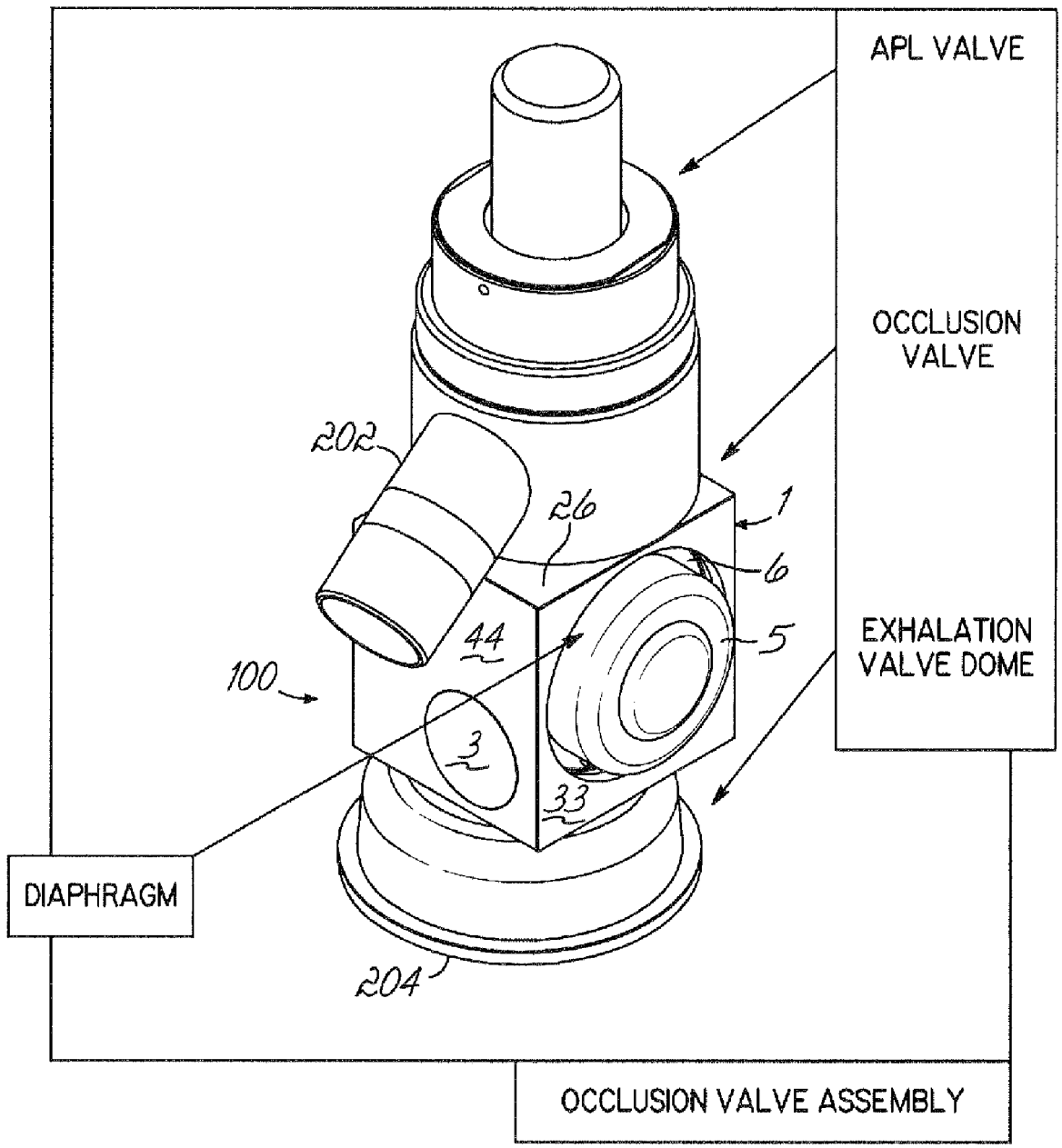
FIG. 34 shows a view of the occlusion valve with safety relief located between the adjustable pressure limiting valve and exhalation valve.
Figure 35:
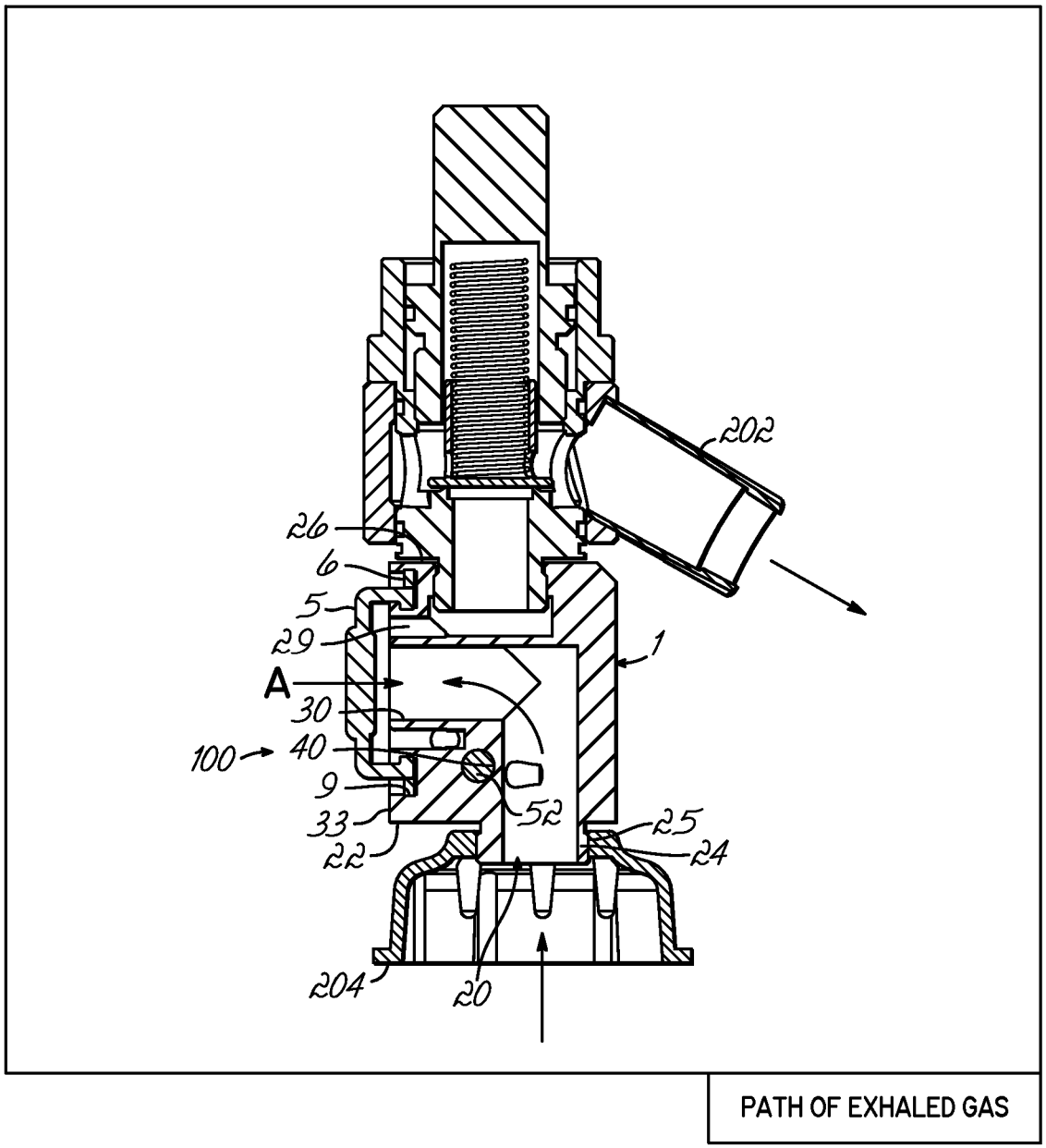
FIG. 35 shows a sectional view of the occlusion valve with safety relief located between the adjustable pressure limiting valve and exhalation valve during exhalation.

The occlusion valve with safety relief 100 is shown generally in FIGS. 1-31 and 34-36. The occlusion valve with safety relief 100 is for use with an anesthesia machine 200, such with such an anesthesia machine 200 being shown schematically in FIGS. 32-33. As shown in FIGS. 34-35, the occlusion valve with safety relief 100 is located between the APL valve 202 and the exhalation valve 204 as shown in FIGS. 34-35, and is threadably joined to each.

Figure 2:
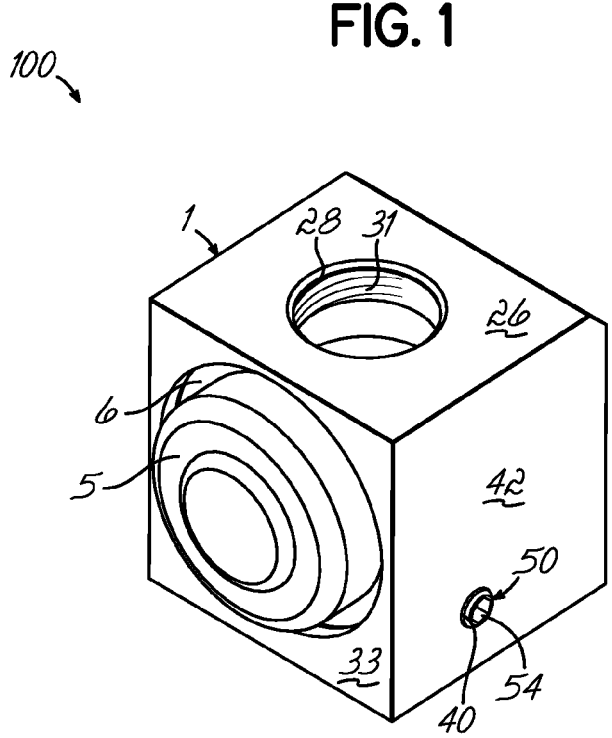
FIG. 2 is a perspective view of the assembled occlusion valve with safety relief.
Figure 3:
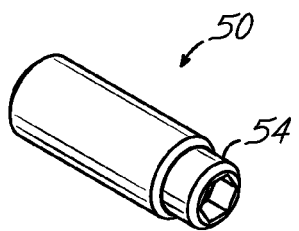
FIG. 3 is an isometric view of the setscrew.
Figure 4:
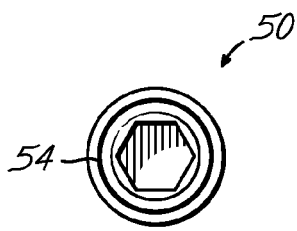
FIG. 4 is a right end elevational view of the setscrew.
Figure 6:
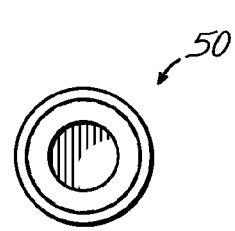
FIG. 6 is a left end elevational view of the setscrew.
Figure 5:
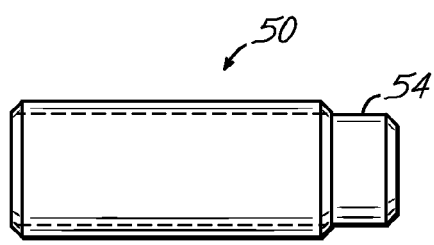
FIG. 5 is a front elevational view of the setscrew.
Figure 7:
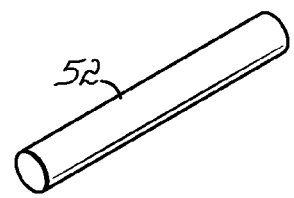
FIG. 7 is an isometric view of the magnet.
Figure 8:
FIG. 8 is a right end view of the magnet.
Figure 9:
FIG. 9 is a front elevational view of the magnet.
Figure 9A:
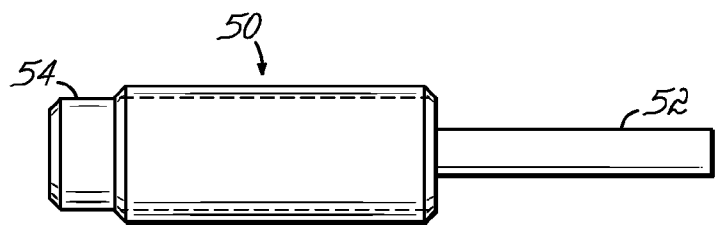
FIG. 9A is a front elevational view of the setscrew joined to the magnet.
Figure 10:
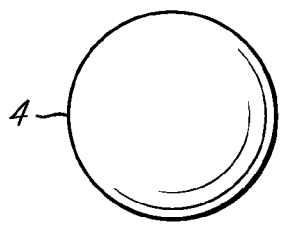
FIG. 10 is a front elevation view of a ball for use in the occlusion valve.
Figure 11:
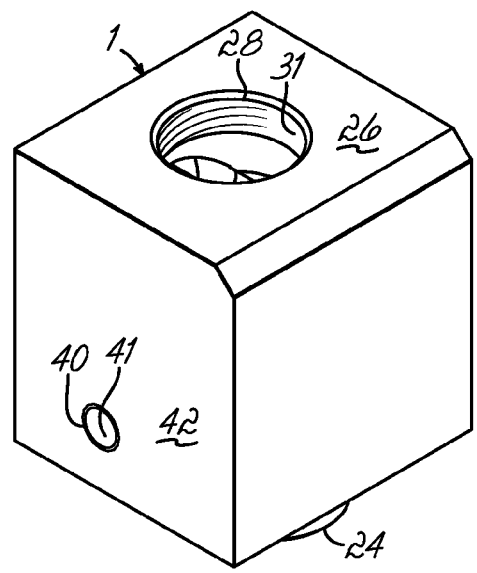
FIG. 11 is a isometric view of a manifold block showing an outlet side thereof.
Figure 12:
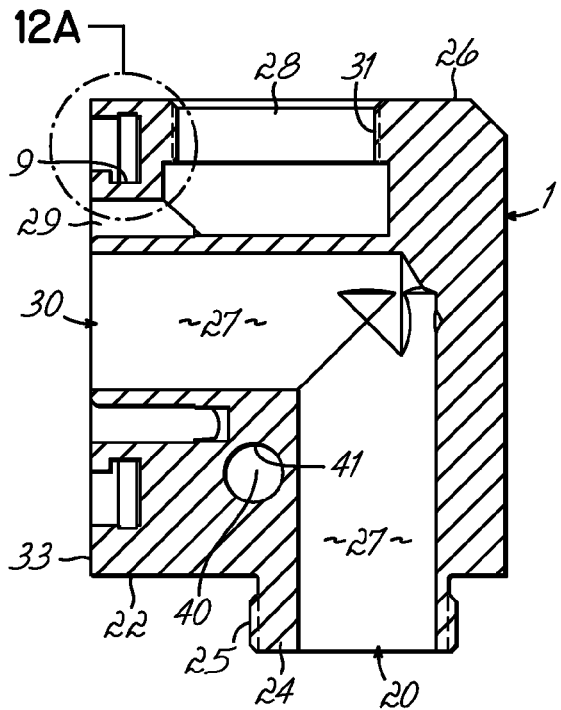
FIG. 12 is a sectional view of the manifold block taken along cut line A-A of FIG. 13.
Figure 13:
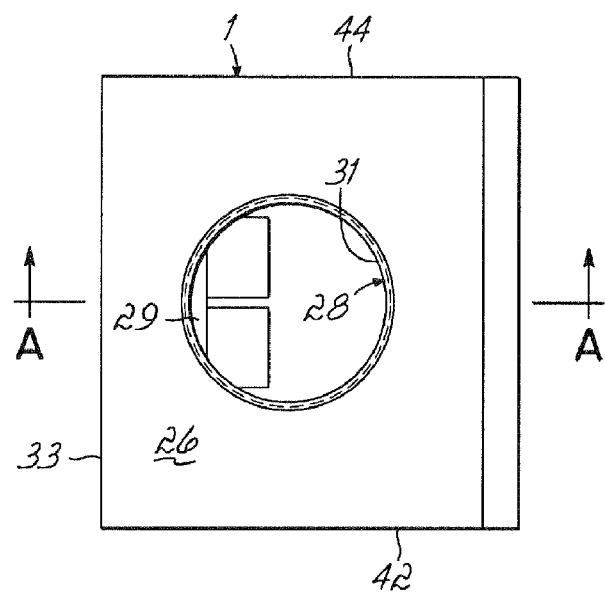
FIG. 13 is a top plan view of the manifold block.
Figure 14:
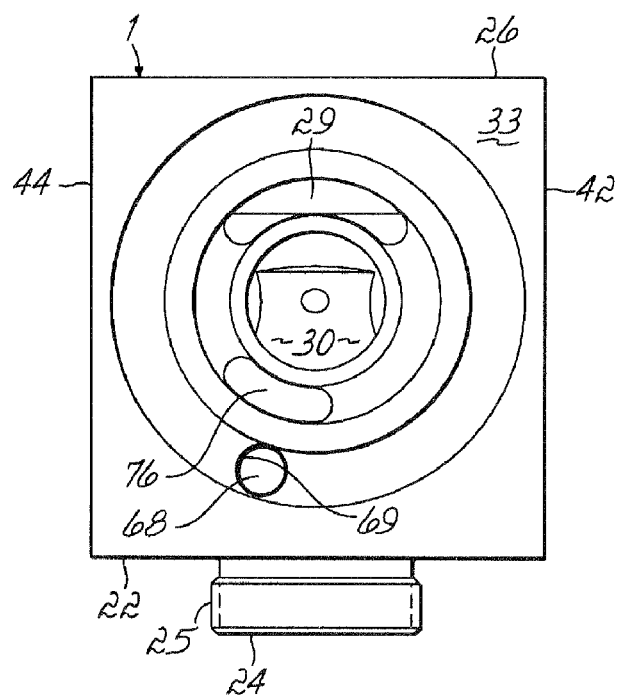
FIG. 14 is a front elevational view of the manifold block.

FIG. 1 shows an exploded view of the occlusion valve with relief 100 which comprises a manifold block 1 that has a generally cubical shape. The manifold block 1 has opposed inlet and outlet sides 22, 26, respectively. The inlet side 22 has an inlet 20, as shown in FIG. 18. An inlet pipe 24 extends from the inlet side 22, as shown in FIGS. 12, 14-17 and 18 and the inlet pipe 24 is for connecting with the exhalation valve 204. In one of the preferred embodiments the inlet pipe 24 has an external thread 25 so that it can be threaded to the exhalation valve 204. FIGS. 2, 11 and 13 show the outlet side 26 of the manifold block 1. The outlet side 26 has an outlet 28 that has an internal thread 31 that threads to the APL valve 202, as shown in FIGS. 34 and 35.

Figure 12A:
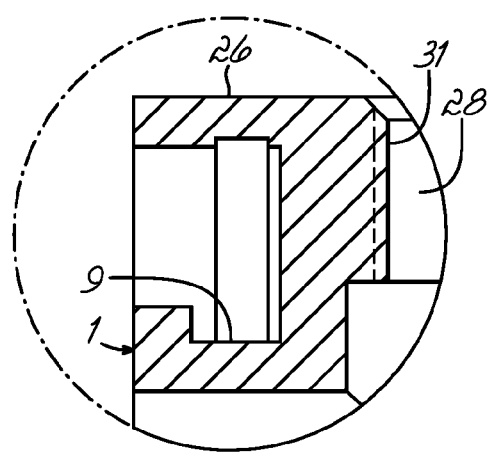
FIG. 12A is an enlarged fragmentary view of a portion of FIG. 12.
Figure 36:
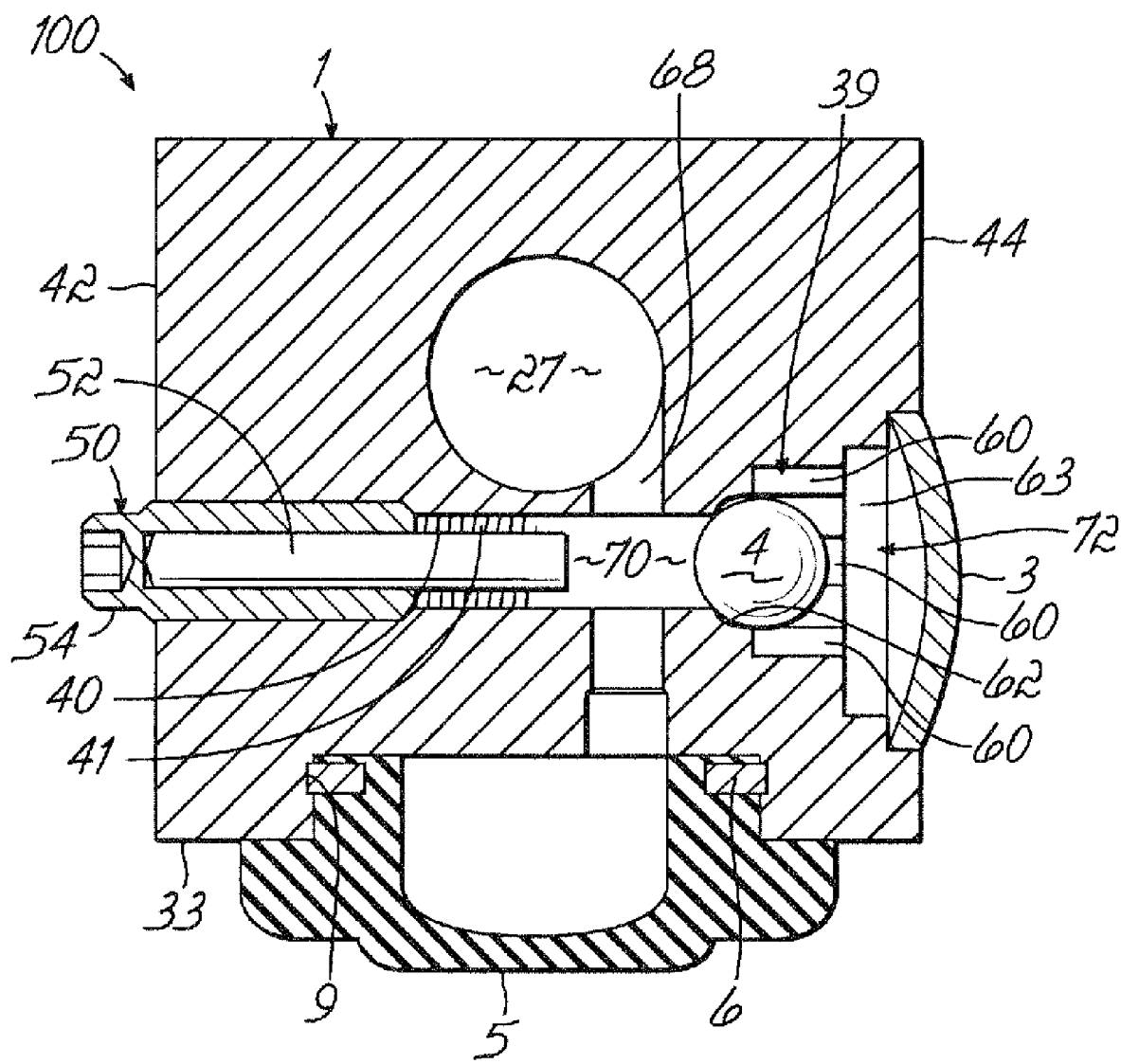
FIG. 36 shows a sectional view of the occlusion valve with safety relief detailing the pressure relief valve.

The manifold block 1 has joined to it a manually operable diaphragm 5 that can be manually pressed and deformed, and that returns to its pre-deformed state when not pressed. The diaphragm 5 is shown in FIGS. 2 and 25-28. As shown in FIGS. 12 and 18, at the inlet 20 there is an inlet passage 27 that extends into the manifold block 1 substantially straight. The inlet passage 27 makes a right angle bend and continues through the manifold block 1 until it ends at a flow opening 30. The flow opening 30 opens on a diaphragm side 33 of the manifold block 1. The diaphragm side 33 of the manifold block 1 extends between the opposed inlet and outlet sides 22, 26, respectively, of the manifold block 1. The diaphragm 5 is joined to the manifold block with a ring 6, as shown in FIGS. 1, 2 and 22, 22A and 23. In particular, and as shown in FIGS. 12-12A and 36, the manifold block 1 is provided with an annular shaped ring lip 9, and the diaphragm 5 is moved adjacent the diaphragm side 33 of the manifold block 1, and the ring 6 is positioned around the diaphragm 5. The ring 6 is forced into the manifold block 1 such that ring 6 engages the annular shaped ring lip 9 formed in the manifold block 1. The diaphragm 5 is thereafter joined to the manifold block 1. The diaphragm 5 comprises a compliant material, for example, plastic, rubber or other suitable material.

The diaphragm 5 is located proximal the flow opening 30 and when the diaphragm 5 is not pressed against the flow opening 30, the diaphragm 5 directs the flow of gas between the diaphragm 5 and the manifold block 1 and out the outlet 28 formed in the manifold block 1. This is the normal flow path of gases or fluids through the manifold block 1. Thus, when the diaphragm 5 is not pressed against the flow opening 30 the gas or fluid entering from the exhalation valve 204 flows from the inlet 20 to the outlet 28 and then to the APL valve 202 relatively unimpeded.

At times it is necessary to pressurize the anesthesia machine 200 to a predetermined pressure. For example, in one of the preferred embodiments, the anesthesia machine 200 is pressurized to a maximum pressure of about 25 cm $H_2O$. To pressurize the anesthesia machine 200, the diaphragm 5 is manually pressed by the user. Pressing the diaphragm 5 closes or seals the flow opening 30, shown in FIG. 12, that is located at the end of the inlet passage 27. Thus, upon pressing the diaphragm 5 no fluid can flow between the diaphragm 5 and the flow opening 30 or to the APL valve 202, and the anesthesia machine 200 can thus advantageously pressurize A pressure relief valve 39 is located internal to the manifold block 1 and is in fluid communication with the inlet and outlet pressures, as shown in FIG. 36. In general, the pressure relief valve 39 includes a magnet 52 and a steel ball 4. The force of magnetic attraction draws the steel ball 4 into contact with a sealing surface or valve seat 62. Then, if downstream pressure exceeds a predetermined maximum pressure, for example, a pressure of about 25 cm $H_2O$, then the pressure relief valve 39 opens and relieves the anesthesia machine at about 25 cm $H_2O$. Thus, when the pressure relief valve 39 opens, downstream gas flows through the pressure relief valve 39 thus advantageously decreasing downstream pressure.

Figure 17:
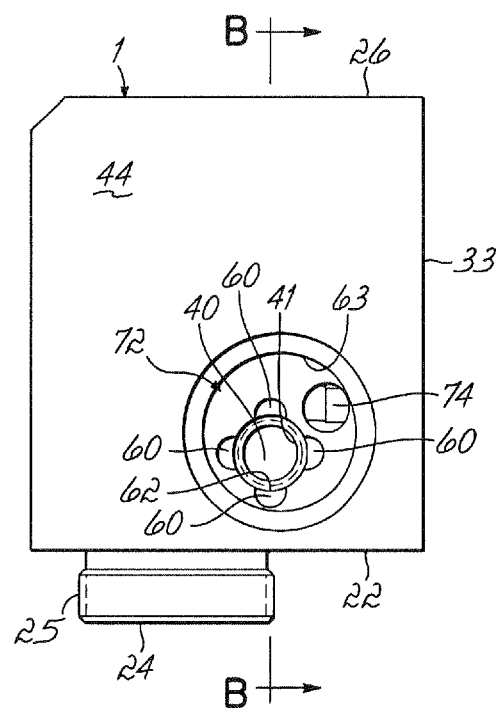
FIG. 17 is a left end elevational view of the manifold block.
Figure 18:
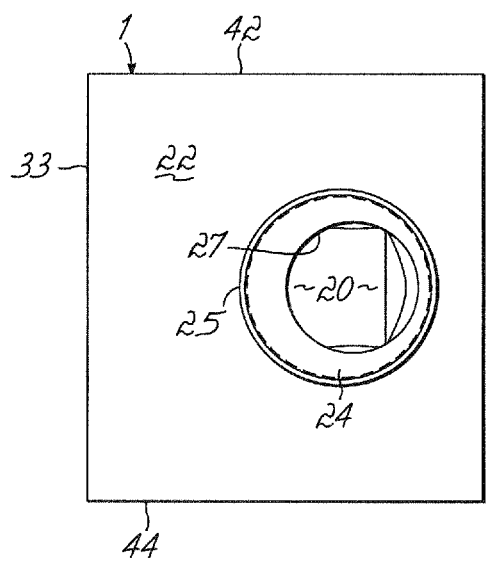
FIG. 18 is a bottom plan view of the manifold block.
Figure 19:
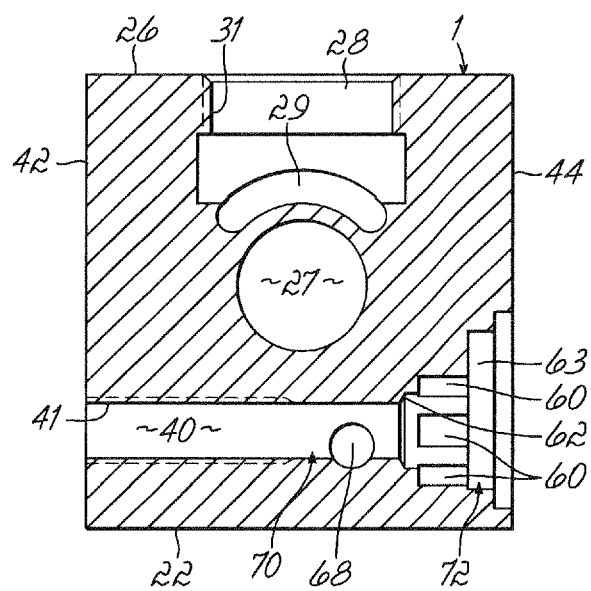
FIG. 19 is a sectional view of the manifold block taken along cut line B-B of FIG. 17.
Figure 20:
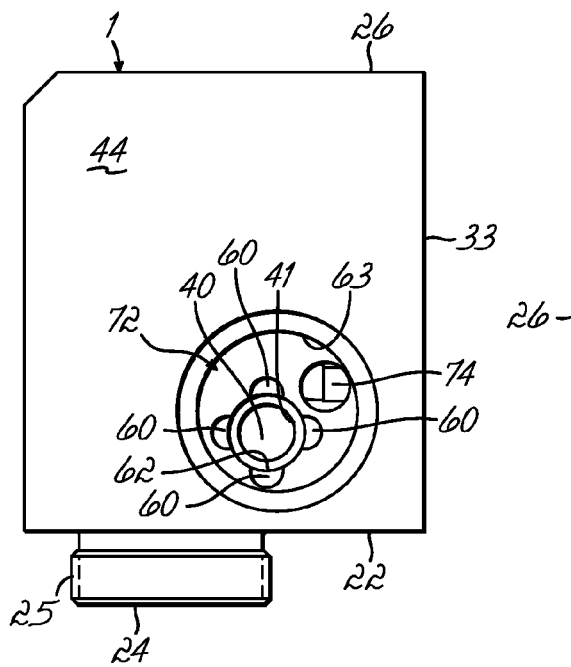
FIG. 20 is a left end elevational view of the manifold block.
Figure 21:
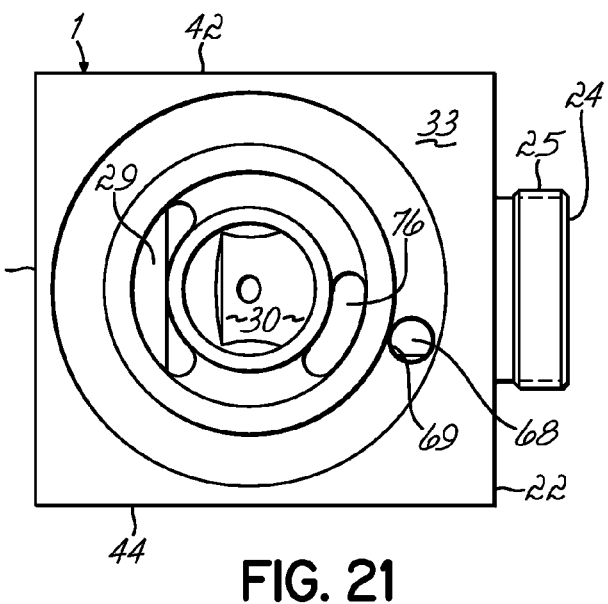
FIG. 21 is a front elevational view of the manifold block.
Figure 22:
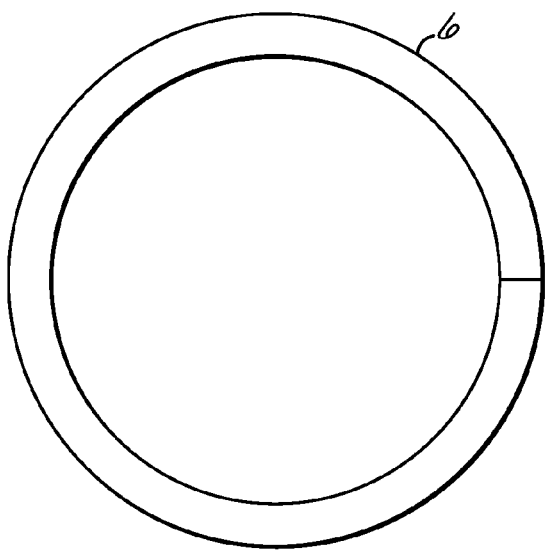
FIG. 22 is a top plan view of the back-up ring.
Figure 23:
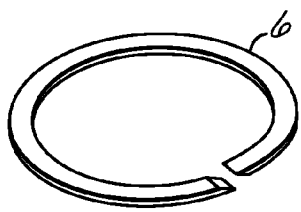
FIG. 23 is an isometric view of the back-up ring.

Turning to FIG. 19, shown therein is a sectional view of the manifold 1 taken along cut line B-B of FIG. 17. FIG. 36 is another sectional view of the manifold block 1 showing the pressure relief valve 39 in greater detail. The manifold block 1 has a bore side 42, as shown in FIGS. 2, 11 and 36, and an opposed capped side 44, as shown in FIGS. 1, 17, 20 and 36. A bore 40 that has an internal thread 41 for part of its length extends into the bore side 42 of the manifold 1, as shown in FIGS. 19 and 36. The internal thread 41 is for threadably receiving an externally threaded setscrew 50 that is joined to the magnet 52, as shown in FIGS. 1, 3-9A, and 36. The magnet 52 can be joined to the setscrew 50 with epoxy, and the magnet 52 has a diameter less than that of the bore 40. The end of the setscrew 50 opposite the magnet 52 has a head 54 that allows the setscrew 50 to be threadably adjusted when threaded in to the internal thread 41 until it is at a desired position internal to the manifold block 1.

The bore 40 extends into the manifold block 1 until it reaches the valve seat or seal surface 62. Counterbores 60 are formed in the manifold block 1 and extend from the valve seat 62 to a steel ball recess 63 formed in a capped side 44 of the manifold block 1, as shown in FIGS. 1, 17, 20 and 36. 63. As previously mentioned, the magnet 52 is for seating the steel ball 4 against the valve seat 62. Thus, by rotating the setscrew 50 the magnet 52 can adjustably moved toward or away from the steel ball 4, and the magnetic force of attraction acting on the steel ball 4 can thus be adjusted. The closer the magnet 52 is to the steel ball 4, the greater the force required to unseat the steel ball 4, and the farther the magnet 52 is from the steel ball 4, the less force required to unset the steel ball 4. Epoxy can be used to lock the setscrew 50 in place once the desired magnetic degree of magnetic attraction between the magnet 52 and steel ball 4 is achieved. In one of the preferred embodiments, the adjustment of the setscrew 52 and the application of the epoxy is carried out at the factory during assembly of the occlusion valve with safety relief 100, so that the desired level of force required to unseat the steel ball 4 can be fixed and not thereafter altered by, for example, an end user. This advantageously keeps the force required to unseat the steel ball 4 a known constant.

Figure 24:
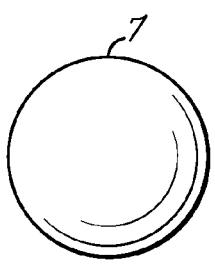
FIG. 24 is a front elevational view of a ball.
Figure 22A:
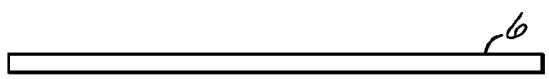
FIG. 22A is a front elevational view of the back-up ring.
Figure 25:
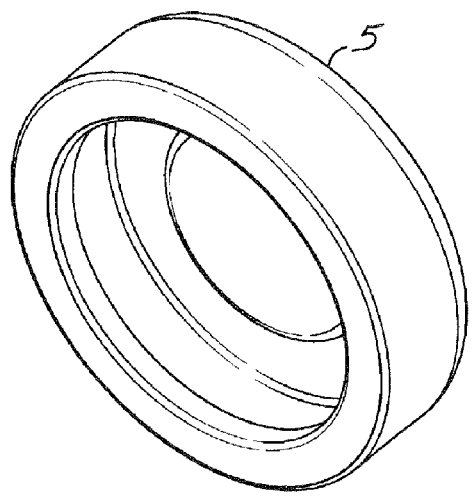
FIG. 25 is an isometric view of the diaphragm.
Figure 26:
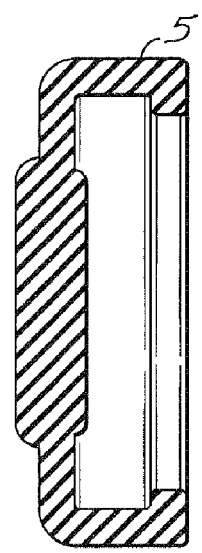
FIG. 26 is a section view of the diaphragm taken along cut line A-A of FIG. 27.
Figure 27:
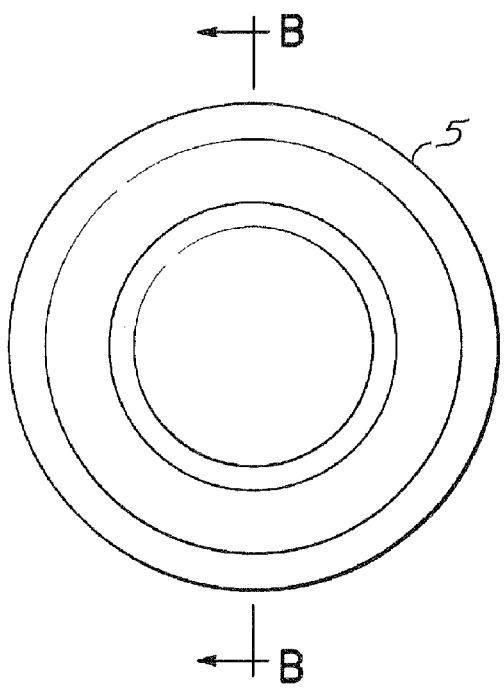
FIG. 27 is a top plan view of the diaphragm.
Figure 28:
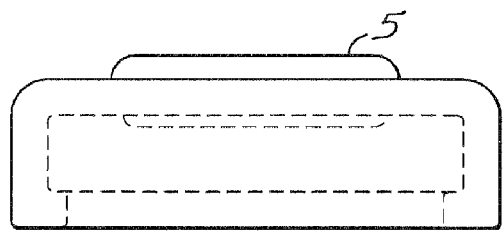
FIG. 28 is a front elevational view of the diaphragm.
Figure 29:
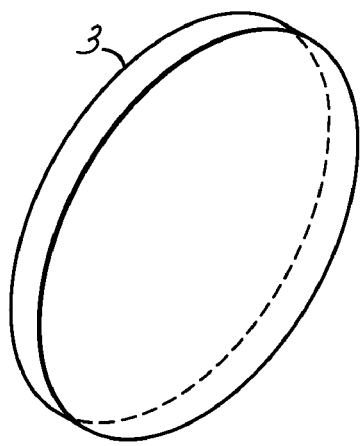
FIG. 29 is an isometric view of an expansion plug.
Figure 30:
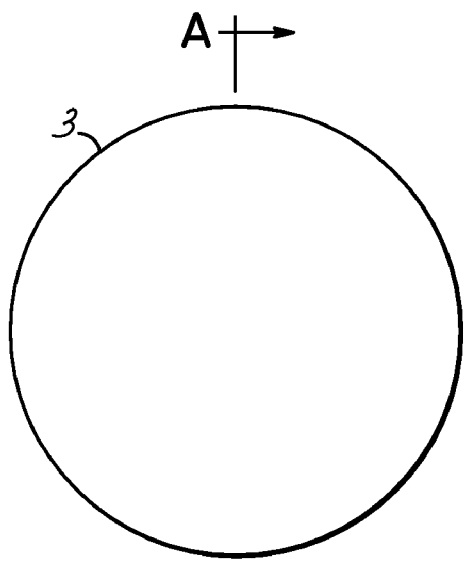
FIG. 30 is a top plan view of the expansion plug.
Figure 31:
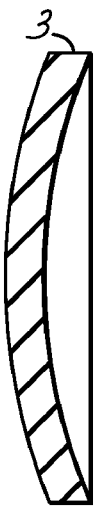
FIG. 31 is a sectional view of the expansion plug taken along cut line A-A of FIG. 30.

In order for downstream pressure to act on the pressure relief 39 the manifold block 1 has a pressure access drilled bore 68, as shown in FIGS. 1, 14, 16, 19 and 21. The pressure access drilled bore 68 extends from the diaphragm side 33 of the manifold block 1, through the manifold block 1 and to the inlet passage 27, such that the pressure access drilled bore 68 is in fluid communication with the inlet passage 27 and thus downstream pressure. A second steel ball 7, as shown in FIGS. 1 and 24, is press fitted into a counterbore 69 formed in the pressure access drilled bore 68 at the diaphragm side 33 of the manifold block 1. The second steel ball 7 is pressed in place, thus sealing one end of the pressure access drilled bore 68.

As shown in FIG. 36, a pressure chamber 70 is defined between the setscrew 50, the steel ball 4, the second steel ball 7 (not shown in FIG. 36) and the surrounding manifold block 1. Downstream fluid or gas can move through the inlet passage 27, through the pressure access drilled bore 68, around the magnet 52 and exert force on the steel ball 4. If the downstream pressure is great enough, that is, reaches the predetermined amount, it will overcome the magnetic force of attraction acting on the steel ball 4 and unseat the steel ball 4 and downstream pressure will be relieved.

Figure 15:
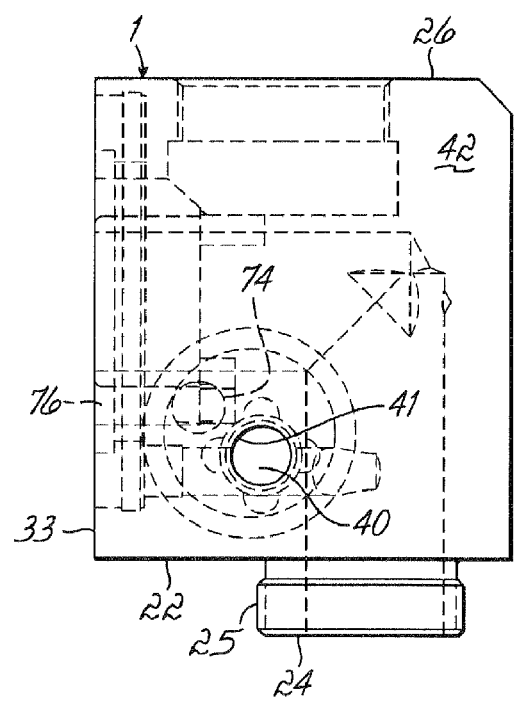
FIG. 15 is a right end elevational view of the manifold block.
Figure 16:
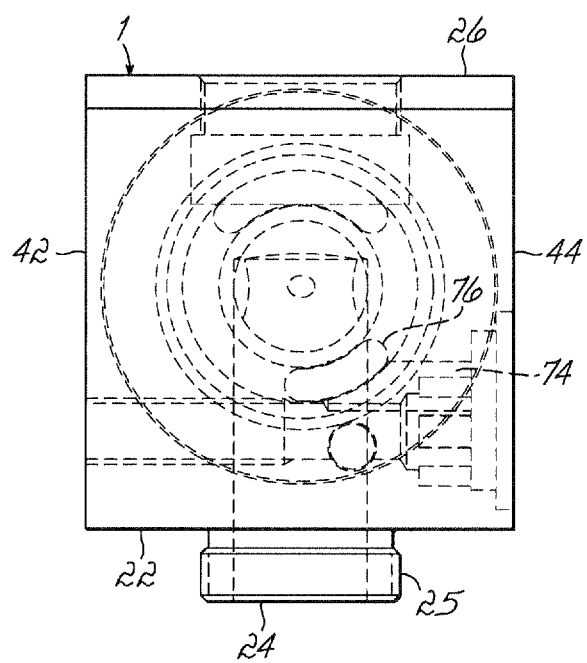
FIG. 16 is a rear elevational view of the manifold block.

As previously mentioned, during normal operation fluid flows from the exhaust valve 204, through the inlet passage 27 of the occlusion valve with safety relief 100 and to the APL valve 202. When the anesthesia machine 200 needs to be pressurized the diaphragm 5 manually pressed by the user. Pressing the diaphragm 5 seals the flow opening 30 at the end of the inlet passage 27. Flow through the through the occlusion valve with safety relief 100 stops and downstream pressure builds. As the pressure in the pressure chamber 70 increases it will eventually reach the predetermined pressure, for example 25 cm H.sub.2O at which pressure the steel ball 4 unseats from the valve seal or seat 62 and downstream pressure is relieved. As shown in FIG. 36, once the steel ball 4 unseats the fluid or gas flows into an expansion plug chamber 72 defined between an expansion plug 3 and the manifold block 1. The expansion plug 3 is shown in detail in FIGS. 29-31 and is joined to the manifold block 1. The gas then flows through an escape passage 74 that leads to an escape slot 76, as shown in FIGS. 15 and 16. The gas then flows between the diaphragm 5 and manifold 1, through the outlet slot 29 shown in FIGS. 14 and 21 and out the outlet 28 shown in FIG. 13.

Thus, the occlusion valve with safety relief 100 advantageously allows a user to press the diaphragm 5 to build downstream pressure to pressurize an anesthesia machine 200, and the occlusion valve with safety relief 100 automatically relieves pressure when downstream pressure reaches a predetermined level and unseats the steel ball 4, even if the user continues to press the diaphragm 5. The occlusion valve with safety relief 100 advantageously eliminates the possibility of a user over-pressurizing the anesthesia machine 200, and advantageously allows an anesthesia machine to be pressurized to a predetermined pressure.

It will be appreciated by those skilled in the art that while an occlusion valve with safety relief has been described above in connection with particular embodiments and examples, the invention is not necessarily so limited, and other embodiments, examples, uses, and modifications and departures from the described embodiments, examples, and uses may be made without departing from the occlusion valve with safety relief. All of these embodiments are intended to be within the scope and spirit of the present invention.

What is claimed is:

1. An occlusion valve with safety relief comprising:
   a manifold block including an inlet and an outlet and a conduit therethrough,
   a valve seat formed in the manifold block between the inlet and the outlet, the valve seat defining an inlet passage on the inlet side of the valve seat and an outlet passage on the outlet side of the valve seat,
   an elastomeric diaphragm connected to the manifold block and for being manually pressed directly by a force applied by a user to the diaphragm from an open condition into a closed condition wherein the diaphragm engages with the valve seat to stop flow between the inlet and the outlet in the closed condition of the diaphragm, the diaphragm being resiliently biased towards the open condition to automatically open the flow between the inlet and the outlet when the diaphragm is not manually pressed, and
   a pressure relief valve in fluid communication with the inlet and outlet passages, wherein when a pressure within the inlet passage exceeds a predetermined amount when the diaphragm is in the closed condition, the pressure relief valve opens to bypass the valve seat and allow flow from the inlet to the outlet through the pressure relief valve.

2. The occlusion valve with safety relief according to claim 1 wherein the pressure relief valve comprises a ball valve.

3. The occlusion valve with safety relief of claim 2, wherein the pressure release valve comprises a magnet and a metal ball, the magnet adapted to attract the metal ball to close the pressure release valve.

4. The occlusion valve with safety relief of claim 1, wherein the diaphragm is formed from a resilient rubber which provides the resilient bias towards the open condition.

5. An occlusion valve with safety relief comprising:
   a manifold block including an inlet and an outlet and a conduit therethrough,
   a valve seat formed in the manifold block between the inlet and the outlet, the valve seat defining an inlet passage on the inlet side of the valve seat and an outlet passage on the outlet side of the valve seat,
   a diaphragm connected to the manifold block so as to be directly accessible externally of the manifold block, the diaphragm being manually pressed from an open condition into a closed condition wherein the diaphragm engages with the valve seat to stop flow between the inlet and the outlet in the closed condition of the diaphragm, the diaphragm being resiliently biased towards the open condition to automatically open the flow between the inlet and the outlet when the diaphragm is not manually pressed, and
   a pressure relief valve in fluid communication with the inlet and outlet passages, wherein when a pressure within the inlet passage exceeds a predetermined amount when the diaphragm is in the closed condition, the pressure relief valve opens to bypass the valve seat and allow flow from the inlet to the outlet through the pressure relief valve.

6. The occlusion valve with safety relief according to claim 5, wherein the pressure relief valve comprises a ball valve.

7. The occlusion valve with safety relief of claim 6, wherein the pressure release valve comprises a magnet and a metal ball, the magnet adapted to attract the metal ball to close the pressure release valve.

8. The occlusion valve with safety relief of claim 5, wherein the diaphragm is formed from a resilient rubber which provides the resilient bias towards the open condition.

* * * * *